US008198051B2

(12) United States Patent
Schicke et al.

(10) Patent No.: US 8,198,051 B2
(45) Date of Patent: Jun. 12, 2012

(54) THERMOCYCLER WITH A TEMPERATURE CONTROL BLOCK DRIVEN IN CYCLES

(75) Inventors: Kirsten Schicke, Kaltenkirchen (DE); Claudia Hofmann, Hamburg (DE)

(73) Assignee: Eppendorf AG, Hamburg (DE)

( * ) Notice: Subject to any disclaimer, the term of this patent is extended or adjusted under 35 U.S.C. 154(b) by 153 days.

(21) Appl. No.: 11/750,745

(22) Filed: May 18, 2007

(65) Prior Publication Data

US 2007/0212774 A1 Sep. 13, 2007

Related U.S. Application Data

(63) Continuation of application No. 10/437,221, filed on May 13, 2003.

(30) Foreign Application Priority Data

May 15, 2002 (DE) ................................. 102 21 763

(51) Int. Cl.
*C12P 19/34* (2006.01)

(52) U.S. Cl. ..................................................... 435/91.2

(58) Field of Classification Search .................. 435/91.1
See application file for complete search history.

(56) References Cited

U.S. PATENT DOCUMENTS

| | | | | |
|---|---|---|---|---|
| 5,525,300 | A * | 6/1996 | Danssaert et al. | 422/99 |
| 5,601,141 | A * | 2/1997 | Gordon et al. | 165/263 |
| 5,871,697 | A * | 2/1999 | Rothberg et al. | 422/68.1 |

FOREIGN PATENT DOCUMENTS

| | | | |
|---|---|---|---|
| AU | 200076605 | | 5/2001 |
| WO | 01/24930 | | 4/2001 |
| WO | WO 0124930 | * | 4/2001 |

* cited by examiner

*Primary Examiner* — Gary Benzion
*Assistant Examiner* — Cynthia Wilder
(74) *Attorney, Agent, or Firm* — Rankin, Hill & Clark LLP

(57) ABSTRACT

A thermocycler comprising a temperature control block (1,2, 3) which is designed to receive several specimens and which is fitted with a control unit (6) that in consecutive cycles applies the different temperature levels (40° C., 70° C., 95° C.) of a PCR procedure to said block, said thermocycler being characterized in that said temperature controlling block is sub-divided into thermally separate segments (1,2,3) each of which is controlled separately and receives several specimens, the control unit (6) being designed to drive the said segments at different cycling rates (nine, seven, four).

7 Claims, 1 Drawing Sheet

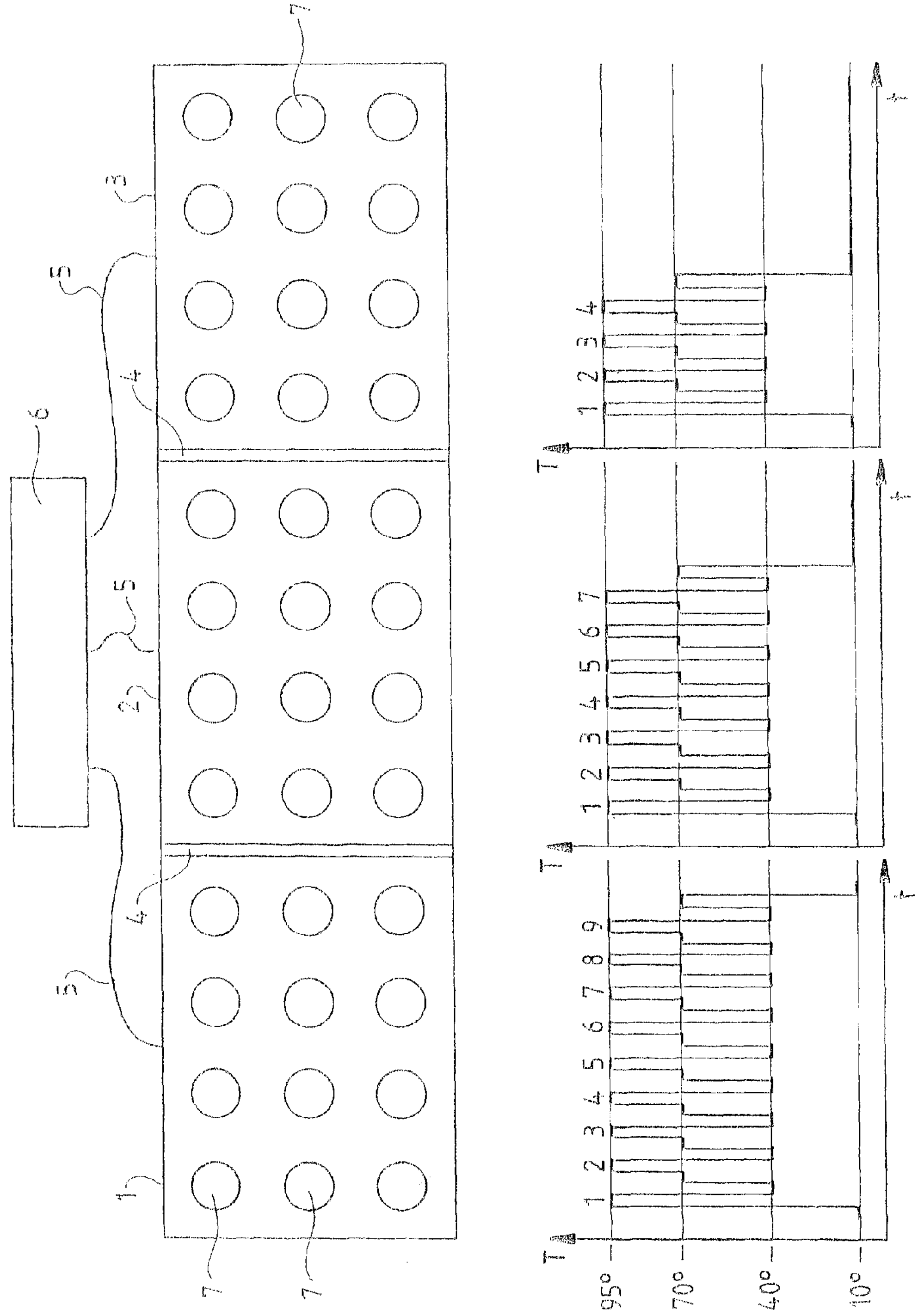
1
2
3
4
5
6
7
T
t
95°
70°
40°
10°

THERMOCYCLER WITH A TEMPERATURE CONTROL BLOCK DRIVEN IN CYCLES

BACKGROUND OF THE INVENTION

The present invention relates to a thermocycler for a PCR procedure.

Thermocyclers have come to be part of the basic equipment of a molecular biology lab. They are used foremost to amplify nucleic acid stretches contained in a probe in low quantity using the Polymerase Chain Reaction (PCR) procedure.

In this procedure, the specimens are sequentially subjected to three temperatures in successive cycles, namely the specimens are in a consecutive manner subjected to the temperature of denaturation of about 95° C., then to the annealing temperature of about 40° C. and then to the elongation temperature of about 70° C. In some special cases, two of theses temperature levels (i.e., the annealing temperature and the elongation temperature) may be consolidated into one temperature level.

Before many specimens can be processed on a large scale, the appropriate PCR parameters must be determined to permit the PCR be performed using optimal parameters. In this respect, it is known to vary both the temperatures at the particular levels and the reagent concentrations. Gradient cyclers are known to make temperature variation easier: these gradient cyclers apply different temperatures at different temperature levels to individual specimens.

It is known moreover that the number of cycles, i.e. the cycling rate, used in a particular PCR procedure may entail different results and hence it should be optimized. In the state of the art, however, optimizing the cycling rate is highly time-consuming because several passes, each with a different cycling rate, must be carried out consecutively in one thermocycler.

SUMMARY OF THE INVENTION

The objective of the present invention is to create a thermocycler that simplifies the optimization of the cycling rate.

The thermocycler of the present invention comprises several block segments operated by means of a control unit, each at a different cycling rate. This design allows operating with several different cycling rates within the conventional range of such cycling rates, that is, illustratively between 10 and 30 cycles, in the individual block segments. This operation is economical in labor in that it takes place in one pass, whereby specimens are made available in the various segments and the specimens are processed at different cycling rates. Other different parameters (such as different concentrations of reagents) may also be employed at the same time in the particular segments for the different specimens in order to make several parameters simultaneously variable. Also, the individual blocks may be designed as gradient blocks so that the particular temperatures levels may be varied concurrently with the cycling rate.

In accordance with the present invention, the individual cycles in all segments may be identical. This design is advantageous because it simplifies the control unit. For instance, the cycles may run in all segments simultaneously and synchronously and, each time, following the cycling rate prescribed for a given segment, the control function applied to that segment is terminated. Next, a cooling temperature of preferably 10° C. is set in order that the specimens be preserved for subsequent analysis.

BRIEF DESCRIPTION OF THE DRAWING

The present invention is shown in illustrative and schematic manner in the appended drawing. The single FIG. 1 shows a thermocycler of the present invention and its related temperature functions.

DETAILED DESCRIPTION OF THE PREFERRED EMBODIMENTS

In substantially schematic manner, FIG. 1 shows a top view of a thermocycler, with its housing, cover and the like removed. Only the temperature control block is shown, which consists of three segments 1, 2 and 3 that, in the shown juxtaposition, are connected to one another by insulating layers 4.

Each segment 1, 2 and 3 is connected by a line 5 to a control unit 6 that may regulate them at the desired temperatures.

In the shown embodiment, the segments 1, 2 and 3 are identical and each is provided with wells 7 in the form of recesses in a thermally conducting and illustratively metallic block. The segments 1, 2 and 3 serve to receive specimens that may be filled directly into these wells 7 or may be contained in conventional plastic vials or be configured on in-situ slides having shapes that match the wells 7. In this illustrative embodiment of the present invention, the wells 7 are configured in each segment 1, 2 and 3 as three rows and four columns.

In a manner not shown, the underside (away from the observer) of segments 1, 2 and 3 of the temperature-control block make contact with appropriate temperature-control elements, such as Peltier elements which, when appropriately driven by the control unit 6, may control the desired temperatures of the segments 1, 2 and 3. For purposes of controlling the temperature of the segments 1, 2 and 3, the temperature control elements may be switched from heating to cooling, such as by reversing the electric current.

In a manner not shown in the drawing, temperature sensors are mounted in the segments 1, 2 and 3, which feed data through lines 5 (which may be multi-wire cables) to the control unit 6 to enable the control unit 6 to accurately set the temperatures of the segments 1, 2 and 3.

A diagrammatic plot (where T denotes the temperature function of time t for the particular temperature that must be set at a given operational pass) is shown in FIG. 1 for each of the segments 1, 2 and 3. The plot is shown below the segments 1, 2 and 3.

In this illustrative embodiment, the control unit 6 is designed in such manner that it may apply four different temperatures to the segments 1, 2 and 3, namely a cooling temperature of 10° C., an annealing temperature of 40° C., an elongation temperature of 70° C. and a denaturing temperature of 95° C. The last three of said temperatures are consecutively applied in consecutive cycles in the way shown in the temperature plot near each segment.

In a first cycle, the temperature of each segment is initially raised to 95° C., then set to 40° C., then at 70° C., whereupon the first cycle is complete. The next cycle again follows at 95° C., 40° C., 70° C. etc. FIG. 1 shows that a total of nine cycles are applied in the first segment 1. At the end of the ninth cycle, the temperature is lowered to the cooling temperature of 10° C., where it remains until the end of the operational pass.

As shown in the adjoining temperature plot, the same cycles are applied in the second segment 2, although they are fewer in number. Only seven cycles are applied. At the end of the seventh cycle, the temperature is lowered to 10° C. As shown in FIG. 1, only four cycles are applied in segment 3.

In the shown, illustrative embodiment of the present invention, the cyclings of the three segments 1, 2 and 3 are synchronous and identical. The only difference is the cycling rate. Upon completing the predetermined number of cycles, and as shown in the temperature plot, cooling is applied in order to preserve the specimens against further heat effects.

Though not shown, the control unit 6 is fitted with adjustment elements by means of which the particular desired cycling rate can be adjusted for the individual segments 1, 2 and 3. Accordingly, operation may be at different cycling rates, for instance at 10, 15 and 20 cycles. Moreover, the same cycling rate may be used in all three segments.

In an alternative embodiment, the segments 1, 2 and 3 may also be in the form of gradient blocks that will apply somewhat different temperatures at one of the temperature levels (such as at the temperature level of 70° C.) to different wells 7 of one or all of the segments. When using such a thermocycler, it will be possible to simultaneously vary in one operational pass both the cycling rate and the temperatures at one temperature level in order to determine the optimum of these two parameters.

What is claimed is:

1. A method for determining an effective cycle rate for amplifying a nucleic acid in a specimen via a polymerase chain reaction procedure, the method comprising the steps of:

providing a thermocycler having a temperature controlled block that is sub-divided into a plurality of segments, and a control unit for controlling the temperature of each segment separately within the controlled block;

placing a portion of the specimen into at least two different segments, said at least two different segments being adjacent to at least one other segment into which a portion of the specimen has been placed;

simultaneously performing the polymerase chain reaction procedure on the portion of the specimen in each of the at least two different segments during which the control unit drives each of the at least two different segments through a predetermined number of temperature cycles, each temperature cycle including a period of time when the segment is maintained at a denaturing temperature followed by a period of time when the segment is maintained at an annealing temperature that is below the denaturing temperature followed by a period of time when the segment is maintained at an elongation temperature that is intermediate of the denaturing temperature and the annealing temperature;

repeating the temperature cycle in each of the at least two different segments a different number of times as compared to the other segment resulting in a different cycle rate for each of the at least two different segments measured as the number of temperature cycles performed for each segment;

using the control unit to drive each segment to a cooling temperature that is below the annealing temperature upon completion of the predetermined number of temperature cycles for each segment, the cooling temperature preserving the portions against further heat affects and for subsequent analysis, wherein at least one segment is driven to the cooling temperature at a time when the other of the at least two different segments is repeating the temperature cycle; and analyzing the portions to determine which cycle rate was most effective at amplifying the nucleic acid in the specimen.

2. The method of claim 1, wherein each of the at least two different segments stops executing temperature cycles at a different time.

3. The method of claim 2, wherein the temperature cycles run in the at least two different segments synchronously until each segment individually completes the predetermined number of temperature cycles allotted to it.

4. The method of claim 1, wherein the cooling temperature is 10° C.

5. The method of claim 1, wherein the controlled block includes a first segment, a second segment and a third segment and wherein the control unit drives the first segment through nine temperature cycles, the second segment through seven temperature cycles and the third segment through four temperature cycles.

6. The method of claim 2, wherein each of the at least two different segments begins executing temperature cycles at the same time.

7. The method of claim 1, wherein the plurality of segments each include a plurality of wells, and wherein the control unit drives the plurality of wells in each segment to a gradient of denaturing temperatures, annealing temperatures and/or elongation temperatures during each temperature cycle.

* * * * *